(12) United States Patent
Mautner

(10) Patent No.: US 7,312,054 B2
(45) Date of Patent: Dec. 25, 2007

(54) METHODS AND REACTION MIXTURE REAGENT FOR INCREASING THE SPECIFICITY AND FIDELITY OF POLYMERASE REACTIONS

(75) Inventor: Martin Eduardo Mautner, Buenos Aires (AR)

(73) Assignee: Biodynamics S.R.L., Buenos Aires (AR)

( * ) Notice: Subject to any disclaimer, the term of this patent is extended or adjusted under 35 U.S.C. 154(b) by 60 days.

(21) Appl. No.: 10/867,994

(22) Filed: Jun. 15, 2004

(65) Prior Publication Data

US 2006/0014152 A1     Jan. 19, 2006

Related U.S. Application Data

(63) Continuation-in-part of application No. 10/316,745, filed on Dec. 11, 2002, now abandoned.

(51) Int. Cl.
  *C12P 19/34* (2006.01)
  *C12Q 1/68* (2006.01)
(52) U.S. Cl. .......................................... 435/91.2; 435/6
(58) Field of Classification Search .................. None
  See application file for complete search history.

(56) References Cited

U.S. PATENT DOCUMENTS 5,976,842 A   11/1999   Wurst 6,171,785 B1   1/2001   Higuchi

FOREIGN PATENT DOCUMENTS

EP   0 512 334 A2 *   11/1992
EP   1 256 631        11/2002

* cited by examiner

*Primary Examiner*—Young J. Kim
(74) *Attorney, Agent, or Firm*—Norris McLaughlin & Marcus, PA

(57) ABSTRACT

A method for reducing the efficiency of primer extension by polymerase enzymes when the 3' end of a primer or growing nucleic acid chain does not hybridize perfectly with the target, for increasing the selectivity of single nucleotide mutation or gene analyses, for suppressing false positive results and for enhancing the fidelity of the amplification of nucleic acid fragments by avoiding the incorporation of mispairs, the method comprising the steps of: (a) obtaining a nucleic acid sample; (b) hybridizing said nucleic acid sample to a primer; (c) subjecting said nucleic acid sample hybridized to a extension reaction by extending a primer with a polymerizing enzyme; and (d) detecting the presence of extension products; wherein the reaction extension mixture medium contains an intercalating agent such as ethidium bromide, dihydroethidium, ethidium homodimer-1, ethidium homodimer-2, acridine, propidium iodide, YOYO®-1 or TOTO®-1. When the intercalating agent is ethidium bromide the concentration is about 1 to 7 g/ml.

13 Claims, 10 Drawing Sheets

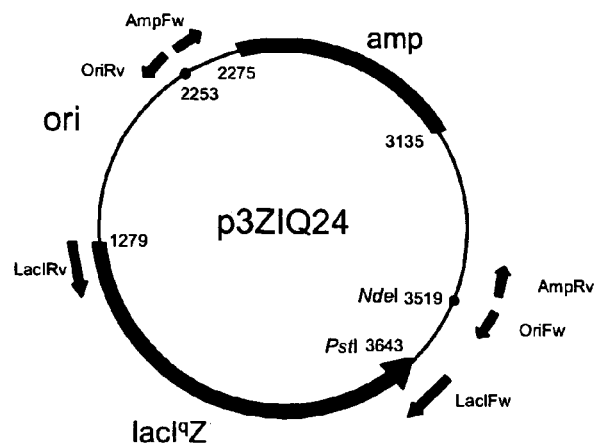
Figure 10-a
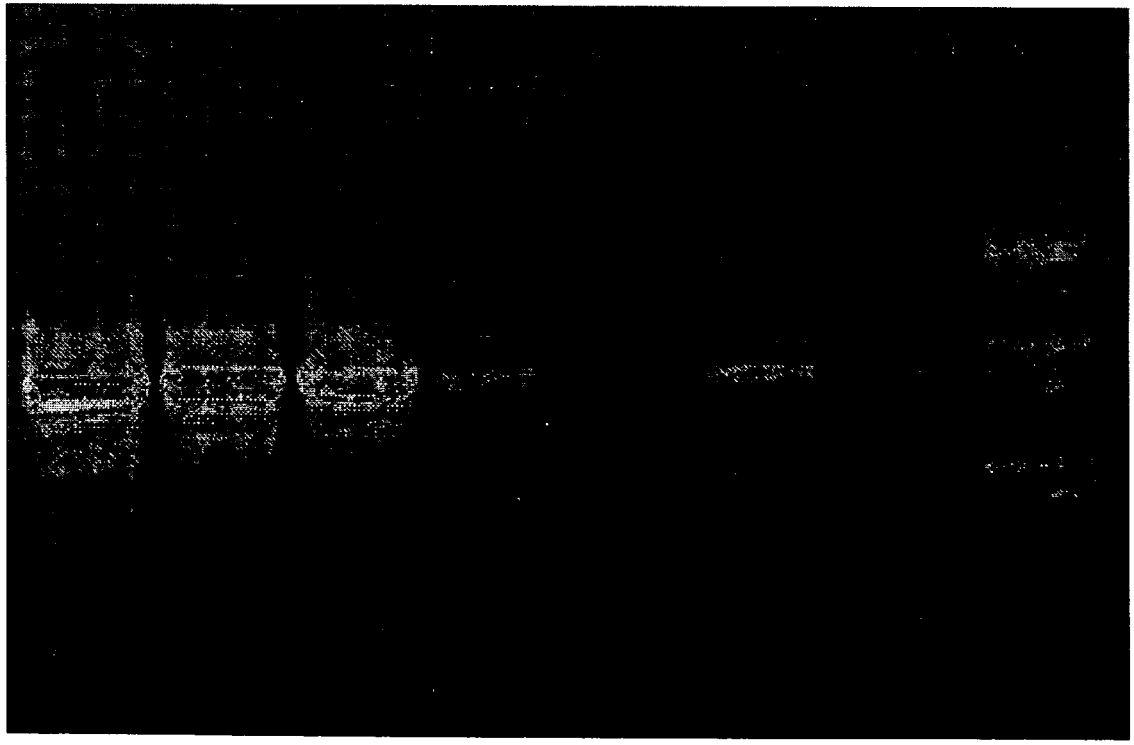
Figure 10-b

US 7,312,054 B2

METHODS AND REACTION MIXTURE REAGENT FOR INCREASING THE SPECIFICITY AND FIDELITY OF POLYMERASE REACTIONS

CROSS REFERENCE TO RELATED APPLICATION

This application is a Continuation in Part of U.S. patent application Ser. No. 10/316,745 entitled "METHODS AND REACTION MIXTURE REAGENT FOR INCREASING THE 3' END SPECIFICITY OF OLIGONUCLEOTIDE PRIMING", filed Dec. 11, 2002 now abandoned.

BACKGROUND OF THE INVENTION

1. Field of the Invention

The present invention relates to the field of molecular biology. The method of the invention is useful to increase both the specificity and the fidelity of PCR or other assays that employ polymerases.

2. Description of the Prior Art

Detecting and identifying variations in DNA sequences among individuals and species has provided insights into evolutionary relationships, inherited disorders, acquired disorders and others aspects of molecular genetic and medicine.

These variations may involve different lengths of DNA, from several nucleotides down to just a single one. The detection of single nucleotide polymorphisms (SNPs) is a challenging task aimed to provide new developments in the field of Molecular Biology.

The analysis of sequence variation has traditionally been performed by restriction fragment length polymorphism (RFLP) in a Southern blot format, or more recently, by digesting PCR products. The RFLP analyses are based on a change in the restriction fragment length as a result of a change in the sequence. Nowadays most techniques rely on the differential annealing of allele-specific oligonucleotides to a template. Some of these techniques are allele-specific oligonucleotide hybridization (ASO), reverse dot blot, competitive oligonucleotide priming (COP), primer extension sequence test (PEST), nucleic acid depolymerization (READIT®), and amplification refractory mutation system (ARMS), also known as allele-specific PCR (ASP), PCR amplification of specific alleles (PASA) and allele-specific amplification (ASA).

A key aspect of the methods that are based upon oligonucleotide base-pairing is that the allele-specific oligonucleotide must anneal only to the homologous sequence to prevent misleading results. However, this is not always the case with the methods where 3' mismatches are used to identify the different alleles. Newton et al. (Nucleic Acids Res. 17: 2503, 1898) and Kwok, et al. (Nucleic Acids Res. 18: 999, 1990) report that a 3' terminal mismatch on the PCR primer produced variable results, making it necessary to add a 3' terminal mismatch accompanied by a second mismatch within the last four nucleotides of the primer. The arbitrariness in the addition of extra mismatches near the 3' end on individual primers in every particular instance limits the general application of the technique in a simple and universal fashion. Also, because of the lower selectivity due to the formation of false DNA synthesis products when using single 3' mismatch primers, the informative power of the gene variation analyses and gene mutation analyses is limited. The formation of false DNA synthesis products can lead to false findings, as a result of which concerning risks arise for the patient and for biomedical research in general.

The U.S. Pat. No. 6,403,313, teaches methods to detect specific hybridization between single-stranded probes and non-denatured double-stranded targets to form triplex by an intercalating agent, thus obviating the need to denature the target. This method can be used to determine the number of mismatched pairs in a hybridization complex, and to map genomes.

Bodmer et. al. (WO 01/75155), teach methods that can distinguish between specific and non-specific amplification products, for example adding to the post-amplification products an amount of small molecules sufficient to increase the pH of the sample products, wherein the pH is 11-14 and then assaying the post-amplification sample product in order to detect and/or quantify any double-stranded nucleic acid present. The method is useful for detecting and/or quantifying a specific double-stranded nucleic acid amplification product in a nucleic amplification reaction post-amplification sample, as in ARMS-PCR methods for SNP typing.

U.S. Pat. No. 5,639,611 discloses an allele specific PCR reaction with two primers (mutant and normal alleles), which one of the primers is complementary to the first allele, but which primer forms a mismatch with the second allele at the 3' end of the primer, employing a DNA polymerase wherein the first allele is specifically amplified but little or no amplification the second allele occurs.

U.S. patent application Ser. No. 10/009,761 disclose a method for detecting a single nucleotide polymorphism in a target by isothermal nucleic acid amplification, hybridizing a detector primer to the target wherein the detector primer comprises a diagnostic nucleotide for the single nucleotide polymorphism about one to four nucleotides from 3' terminal nucleotide of the detector primer, which is complementary to the target sequence, amplifying the target, determining an efficiency of detector primer extension and detecting de presence or absence of the single nucleotide polymorphism based on the efficiency of detector primer extension. This application disclosed the ARMS method.

U.S. Pat. No. 6,312,894 disclosed an hybridization and mismatch discrimination using oligonucleotides conjugated to minor grooves binders. The minor grooves binders is a molecule having a molecular weight of approximately 150 to 2,000 Daltons as 1,2-dihydro-(3H)-pyrrolo[3,2-e]indole-7-carboxylate that binds in a non-intercalating manner into de minor groove of a double-stranded nucleic acid.

On the other hand, the use of high fidelity DNA polymerases in the polymerase chain reaction (PCR) is essential for reducing errors in the amplification of products that are intended for cloning, sequencing and expression. Several DNA Polymerases with 3'-5' exonuclease proofreading activity (Pfu, Vent, Deep Vent) are currently used for such high fidelity applications. However, Taq DNA polymerase, which is the most used enzyme in routine PCR, does not have a proofreading activity and shows a fairly low fidelity (Tindall, K. R. and Kunkel, T. A. (1988) *Biochemistry* 28:6008). Some improvements on the fidelity of Taq DNA polymerase have been reported using pH 5-6 or equimolar concentrations of $MgCl_2$ and dNTPs (Eckert, K. A. and Kunkel, T. A. (1990) *Nucl. Acids. Res.* 18:3739).

It would be therefore convenient to have a method to increase the selectivity of gene variation analyses and, by suppressing the formation of false positives, to prevent wrong diagnoses and erroneous findings. The goal of the present invention is to increase the selectivity in specific nucleic acids sequence analyses adding an intercalating agent to the conventional reactions medium, reducing the efficiency of primer extension by polymerase when the 3' end of a primer does not hybridize perfectly with the target sequence. The addition of the intercalating agent avoids the need to place a second mismatch in the sequence of the detector primer which is not directed to detection or identification of the allele of interest. Since the priming selectivity repeats in every following nucleotide addition to the growing chain, it is also another embodiment of the present invention to increase the fidelity of the amplification of nucleic acid fragments, in particular, those which will be used in cloning, expression and all other applications where overall low error rates in nucleic acid chains may be desired.

SUMMARY OF THE INVENTION

It is therefore an object of the present invention to provide a method for increasing the selectivity of primer extension by polymerase enzymes when the 3' end of the initial primer or the growing, priming strand does not hybridize perfectly with the target, increasing the selectivity of single nucleotide mutation or gene analyses by suppressing false positive results and enhancing the fidelity of the polymerase reaction by avoiding the incorporation of mispairs, comprising the steps of:

(a) obtaining a nucleic acid sample;

(b) hybridizing said nucleic acid sample to a primer;

(c) subjecting said nucleic acid sample hybridized to a extension reaction by extending the primer with a polymerizing enzyme, wherein the reaction extension mixture medium contains an intercalating agent; and (d) detecting the presence of extension products.

In a preferred embodiment the methods comprises: (a) obtaining a nucleic acid sample; (b) hybridizing said nucleic acid sample to primer pair by subjecting said nucleic acid sample hybridized to a PCR, wherein the PCR reaction mixture contains an intercalating agent; and (c) detecting the presence of amplification products The intercalating agent may be any intercalating agent as ethidium bromide, dihydroethidium, ethidium homodimer-1, ethidium homodimer-2, acridine, propidium iodide, YOYO®-1 [Invitrogen Corporation, 1600 Faraday Avenue, PO Box 6482, Carlsbad, Calif. 92008, blue light fluorescent nucleic acid dye], TOTO®-1 [Invitrogen Corporation, 1600 Faraday Avenue, PO Box 6482, Carlsbad, Calif. 92008, fluorescent nucleic acid dye], or any other flat organic molecule capable of stacking between the nucleic acid bases. In a preferred embodiment the intercalating agent is ethidium bromide at a concentration about 1 to 7 µg/ml.

The methods of the present invention decrease the amount of extension products when the 3' end of a primer or growing nucleic acid chain does not hybridize perfectly with the target sequence, increase the selectivity detection of single nucleotide mutation and/or suppress false positive extension products in gene analyses and/or decrease the error rate in PCR amplifications.

It is still another object of the present invention to provide a reaction extension mixture reagent, wherein the reagent comprises: a polymerizing enzyme, dNTPs, a buffer, an intercalating agent as for example ethidium bromide, dihydroethidium, ethidium homodimer-1, ethidium homodimer-2, acridine, propidium iodide, YOYO®-1, TOTO®-1, or any other flat organic molecule capable of stacking between the nucleic acid bases.

The reaction extension mixture reagent may be a PCR reaction mixture or any medium which an extension reaction of nucleic acid was made.

The above and other objects, features and advantages of this invention will be better understood when taken in connection with the accompanying drawings and description.

BRIEF DESCRIPTION OF THE DRAWINGS

The present invention is illustrated by way of example in the following drawings wherein.

Figure 2:
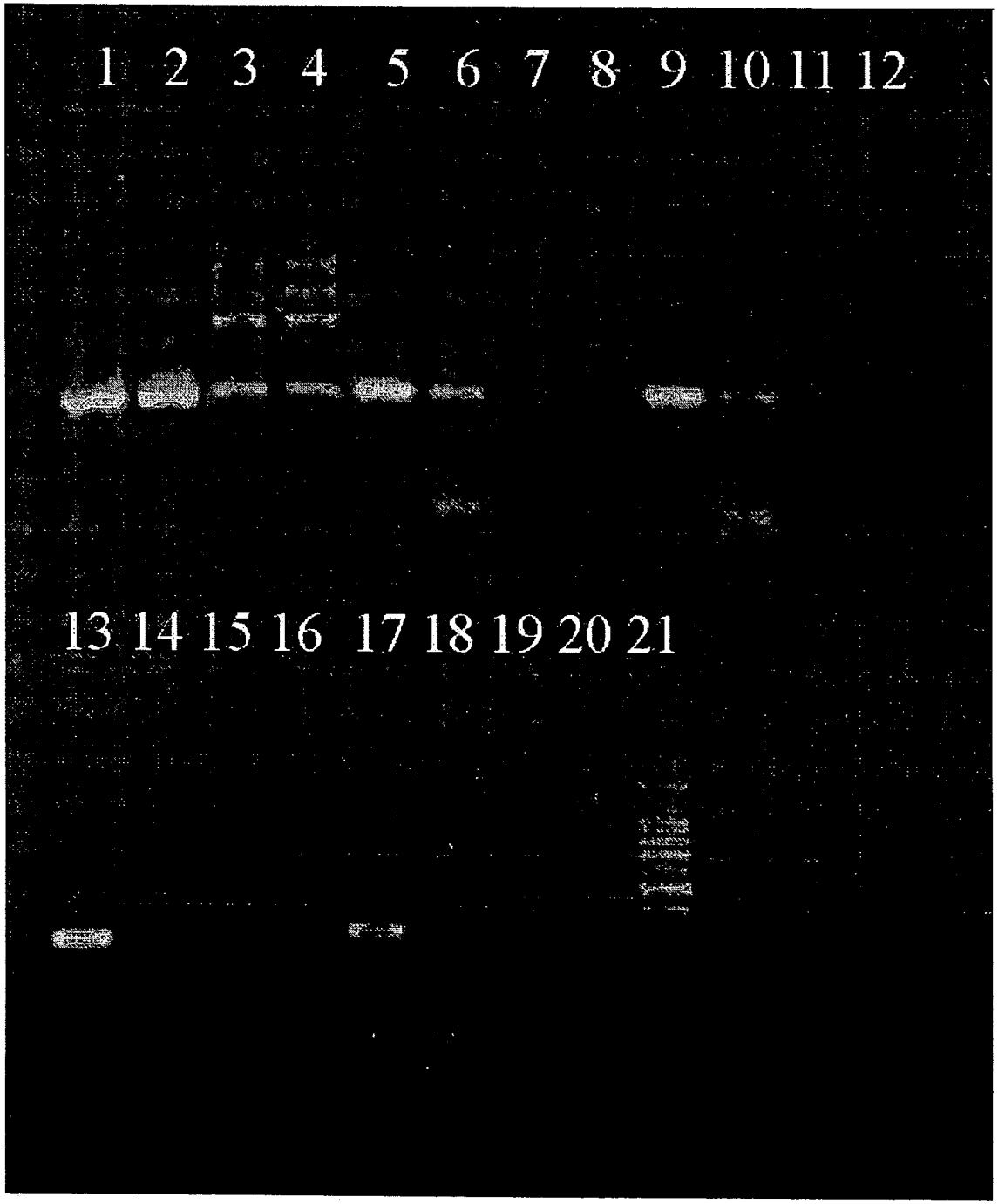

Lane 1 through 4: 16311A (SEQ ID NO:3), 16311G (SEQ ID NO:4), 16311T (SEQ ID NO:5) and 16311C (SEQ ID NO:6) without ethidium bromide. Lane 5 through 8: 16311A (SEQ ID NO:3), 16311G (SEQ ID NO:4), 16311T (SEQ ID NO:5) and 16311C (SEQ ID NO:6) with 4.5 µg/ml ethidium bromide. Lane 9 through 12: 16311A (SEQ ID NO:3), 16311G (SEQ ID NO:4), 16311T (SEQ ID NO:5) and 16311C (SEQ ID NO:6) with 5.0 µg/ml ethidium bromide. Lane 13 through 16: 16311A (SEQ ID NO:3), 16311G (SEQ ID NO:4), 16311T (SEQ ID NO:5) and 16311C (SEQ ID NO:6) C with 5.5 µg/ml ethidium bromide. Lane 16 through 20: 16311A (SEQ ID NO:3), 16311G (SEQ ID NO:4), 16311T (SEQ ID NO:5) and 16311C (SEQ ID NO:6) with 6.0 µg/ml ethidium bromide. Lane 21: 100 bp ladder (Promega Corp.);

FIG. 2 shows the amplification results on mtDNA in 2% agarose gel stained with ethidium bromide showing the amplification results on mtDNA carrying an Andersons' T nucleotide at position 16311 using primers FW I and either 16311A (SEQ ID NO:3), 16311G (SEQ ID NO:4), 16311T (SEQ ID NO: 5) or 16311C (SEQ ID NO:6) at different ethidium bromide concentrations.

Figure 3:

Lane 1 through 4: 16311A (SEQ ID NO:3), 16311G (SEQ ID NO:4), 16311T (SEQ ID NO:5) and 16311C (SEQ ID NO:6) without ethidium bromide. Lane 5 through 8: 16311A (SEQ ID NO:3), 16311G (SEQ ID NO:4), 16311T (SEQ ID NO:5) and 16311C (SEQ ID NO:6) with 4.5 µg/ml ethidium bromide. Lane 9 through 12: 16311A (SEQ ID NO:3), 16311G (SEQ ID NO:4), 16311T (SEQ ID NO:5) and 16311C (SEQ ID NO:6) with 5.0 µg/ml ethidium bromide. Lane 13 through 16: 16311A (SEQ ID NO:3), 16311G (SEQ ID NO:4), 16311T (SEQ ID NO:5) and 16311C (SEQ ID NO:6) with 5.5 µg/ml ethidium bromide. Lane 16 through 20: 16311A (SEQ ID NO:3), 16311G (SEQ ID NO:4), 16311T (SEQ ID NO:5) and 16311C (SEQ ID NO:6) with 6.0 µg/ml ethidium bromide. Lane 21: 100 bp ladder (Promega Corp);

FIG. 3 shows the amplification results on mtDNA in a 2% agarose gel stained with ethidium bromide showing the amplification results on mtDNA carrying a C nucleotide at position 16256 using primers FW I and either 16256A (SEQ ID NO:7), 16256G (SEQ ID NO:8), 16256T (SEQ ID NO:9) or 16256C (SEQ ID NO:10) at different ethidium bromide concentrations.

Figure 4:
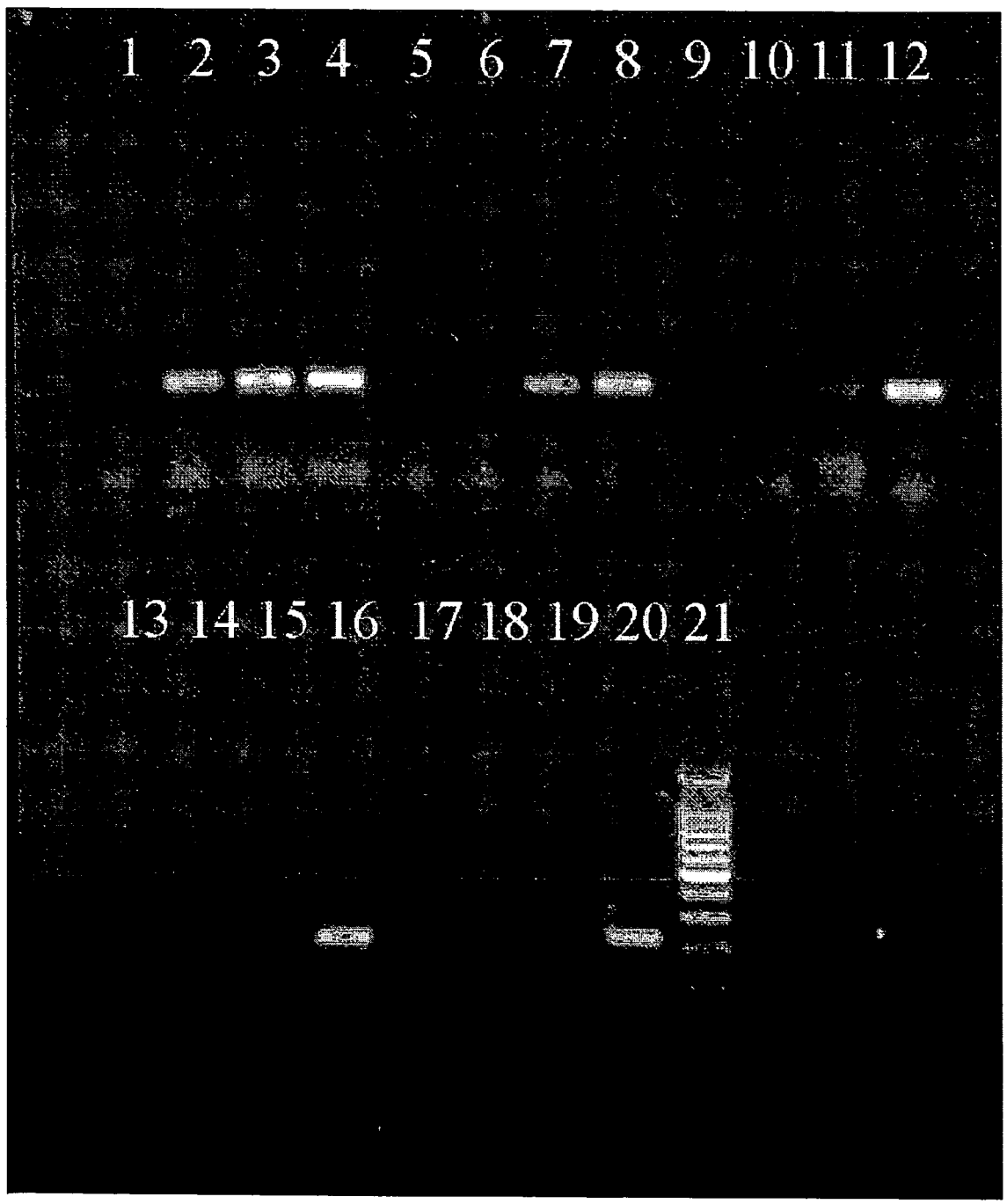

Lane 1 through 4: 16256A (SEQ ID NO:7), 16256G (SEQ ID NO:8), 16256T (SEQ ID NO:9) and 16256C (SEQ ID NO:10) without ethidium bromide. Lane 5 through 8: 16256A (SEQ ID NO:7), 16256G (SEQ ID NO:8), 16256T (SEQ ID NO:9) and 16256C (SEQ ID NO:10) with 4.5 µg/ml ethidium bromide. Lane 9 through 12: 16256A (SEQ ID NO:7), 16256G (SEQ ID NO:8), 16256T (SEQ ID NO:9) and 16256C (SEQ ID NO:10) with 5.0 µg/ml ethidium bromide. Lane 13 through 16: 16256A (SEQ ID NO:7), 16256G (SEQ ID NO:8), 16256T (SEQ ID NO:9) and 16256C (SEQ ID NO:10) with 5.5 µg/ml ethidium bromide. Lane 16 through 20: 16256A (SEQ ID NO:7), 16256G (SEQ ID NO:8), 16256T (SEQ ID NO:9) and 16256C (SEQ ID NO:10) with 6.0 µg/ml ethidium bromide. Lane 21: 100 bp ladder (Promega Corp.);

FIG. 4 shows the amplification results on mtDNA in 2% agarose gel stained with ethidium bromide showing the amplification results on mtDNA carrying a G nucleotide at position 143 using primers FW II (SEQ ID NO:2) and either 143A (SEQ ID NO:11), 143G (SEQ ID NO:12), 143T (SEQ ID NO:13) or 143C (SEQ ID NO:14) at different ethidium bromide concentrations.

Lane 1 through 4: 143A (SEQ ID NO:11), 143G (SEQ ID NO:12), 143T (SEQ ID NO:13) and 143C (SEQ ID NO:14) without ethidium bromide. Lane 5 through 8: 143A (SEQ ID NO:11), 143G (SEQ ID NO:12), 143T (SEQ ID NO:13) and 143C (SEQ ID NO:14) with 4.5 µg/ml ethidium bromide. Lane 9 through 12: 143A (SEQ ID NO:11), 143G (SEQ ID NO:12), 143T (SEQ ID NO:13) and 143C (SEQ ID NO:14) with 5.0 µg/ml ethidium bromide. Lane 13 through 16: 143A (SEQ ID NO:11), 143G (SEQ ID NO:12), 143T (SEQ ID NO:13) and 143C (SEQ ID NO:14) with 5.5 µg/ml ethidium bromide. Lane 16 through 20: 143A (SEQ ID NO:11), 143G (SEQ ID NO:12), 143T (SEQ ID NO:13) and 143C (SEQ ID NO:14) with 6.0 µg/ml ethidium bromide. Lane 21: 100 bp ladder (Promega Corp.)

Figure 5:

FIG. 5 shows the amplification results on mtDNA in 2% agarose gel stained with ethidium bromide showing the amplification results on mtDNA carrying a T to C transition at position 16311 with 5.0 µg/ml ethidium bromide using primers FW I and either 16311A (SEQ ID NO:3) or 16311G (SEQ ID NO:4) at different concentrations of downstream primers. Lane 1 through 2: 100 pmole of 16311A (SEQ ID NO:3) and 16311G (SEQ ID NO:4) and 5.0 µg/ml ethidium bromide.

Lane 3 through 4: 50 pmole 16311A (SEQ ID NO:3) and 16311G (SEQ ID NO:4), 5.0 µg/ml ethidium bromide. Lane 5 through 6: 5 pmole 16311A (SEQ ID NO:3) and 16311G (SEQ ID NO:4), 5.0 µg/ml of ethidium bromide. Lane 7 through 8: 2.5 pmole 16311A (SEQ ID NO:3) (SEQ ID NO:3) and 16311G (SEQ ID NO:4), 5.0 µg/ml ethidium bromide. Lane 9 through 10: 0.5 pmole 16311A (SEQ ID NO:3), (SEQ ID NO:3) and 16311G (SEQ ID NO:4), 5.0 µg/ml ethidium bromide. Lane 11: 100 bp ladder (Promega Corp.). Lane 13 through 14: 100 pmole 16311A (SEQ ID NO:3) and 16311G (SEQ ID NO:4), without ethidium bromide. Lane 15 through 16: 50 pmole 16311A (SEQ ID NO:3) and 16311G (SEQ ID NO:4), without ethidium bromide. Lane 17 through 18: 5 pmole 16311A (SEQ ID NO:3) and 16311G (SEQ ID NO:4), without ethidium bromide. Lane 19 through 20: 2.5 pmole 16311A (SEQ ID NO:3), and 16311G (SEQ ID NO:4), without ethidium bromide. Lane 21 through 22: 0.5 pmole 16311A (SEQ ID NO:3) and 16311G (SEQ ID NO:4), without ethidium bromide. Lane 23: 100 bp ladder (Promega Corp.).

Figure 6:
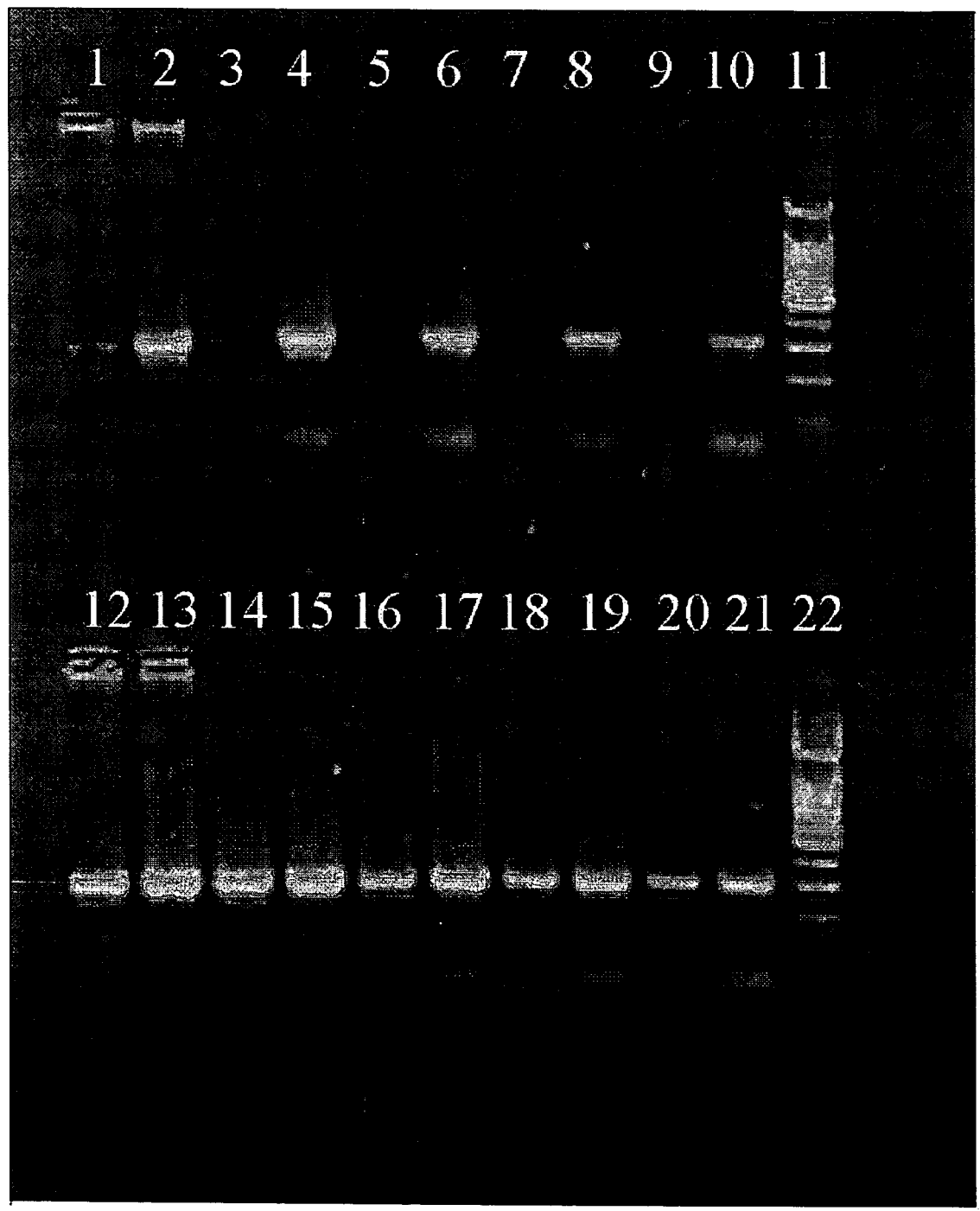

FIG. 6 shows the amplification results on mtDNA in 2% agarose gel stained with ethidium bromide showing the amplification results on mtDNA carrying a T to C transition at position 16311 with 5.0 µg/ml ethidium bromide using primers FW I and either 16311A (SEQ ID NO:3) or 16311G (SEQ ID NO:4) at different concentrations of template.

Lane 1 and 2: 16311A (SEQ ID NO:3) and 16311G (SEQ ID NO:4) at 500 ng total DNA, 5.0 g/ml ethidium bromide. Lane 3 and 4: 16311A (SEQ ID NO:3) and 16311G (SEQ ID NO:4) at 50 ng total DNA, 5.0 µg/ml ethidium bromide. Lane 5 and 6: 16311A (SEQ ID NO:3) and 16311G (SEQ ID NO:4) at 10 ng total DNA, 5.0 µg/ml ethidium bromide. Lane 7 and 8: 16311A (SEQ ID NO:3) and 16311G (SEQ ID NO:4) at 2 ng total DNA, 5.0 µg/ml ethidium bromide. Lane 9 and 10: 16311A (SEQ ID NO:3) and 16311G (SEQ ID NO:4) at 0.5 ng total DNA, 5.0 µg/ml ethidium bromide. Lane 11: 100 bp ladder (Promega Corp.). Lane 13 and 14: 16311A (SEQ ID NO:3) and 16311G (SEQ ID NO:4) at 500 ng total DNA, without ethidium bromide. Lane 15 and 16: 16311A (SEQ ID NO:3) and 16311G (SEQ ID NO:4) at 50 ng total DNA, without ethidium bromide. Lane 17 and 18: 16311A (SEQ ID NO:3) and 16311G (SEQ ID NO:4) at 10 ng total DNA, without ethidium bromide. Lane 19 and 20: 16311A (SEQ ID NO:3) and 16311G (SEQ ID NO:4) at 2 ng total DNA, without ethidium bromide. Lane 21 and 22: 16311A (SEQ ID NO:3) and 16311G (SEQ ID NO:4) at 0.5 ng total DNA, without ethidium bromide. Lane 23: 100 bp ladder (Promega Corp.).

Figure 7:
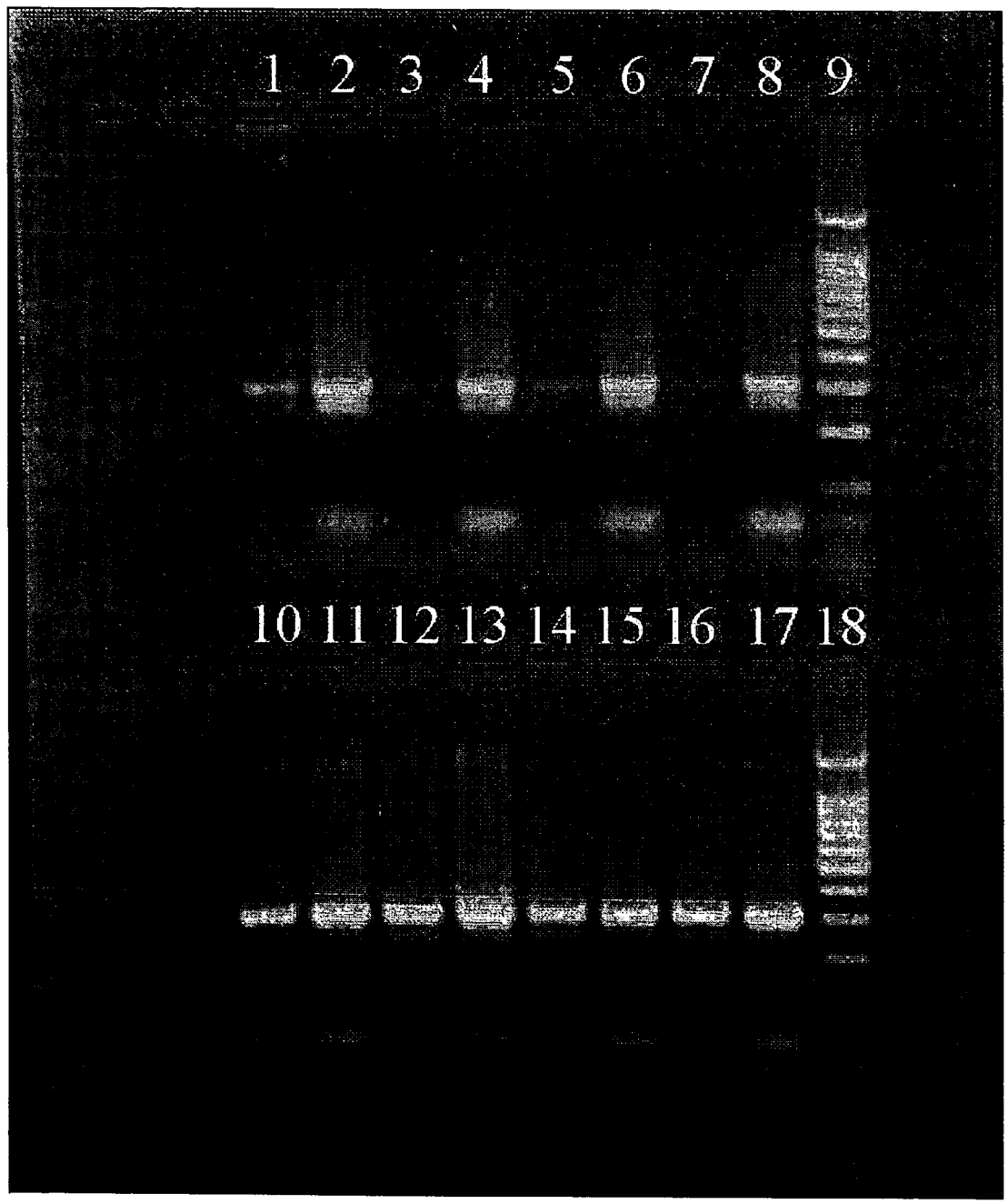

FIG. 7 shows the amplification results on mtDNA in 2% agarose gel stained with ethidium bromide showing the amplification results on mtDNA carrying a T to C transition at position 16311 with primers FW I and either 16311A (SEQ ID NO:3) or 16311G (SEQ ID NO:4) adding 5.0 µg/ml ethidium bromide before, in between and after the primers and the template.

Lane 1 and 2: 16311A (SEQ ID NO:3) and 16311G (SEQ ID NO:4) with 5.0 µg/ml ethidium bromide added after the primers and the template. Lane 3 and 4: 16311A (SEQ ID NO:3) and 16311G (SEQ ID NO:4) with 5.0/g/ml ethidium bromide added after the template and before the primers. Lane 5 and 6: 16311A (SEQ ID NO:3) and 16311G (SEQ ID NO:4) with 5.0 µg/ml ethidium bromide added before the primers and the primers template. Lane 7 and 8: 16311A (SEQ ID NO:3) and 16311G (SEQ ID NO:4) with 5.0 µg/ml ethidium bromide added after the primers and before the template. Lane 9: 100 bp ladder (Promega Corp.). Lane 10 and 11: 16311A (SEQ ID NO:3) and 16311G (SEQ ID NO:4) with water added after the primers and the template. Lane 12 and 13: 16311A (SEQ ID NO:3) and 16311G (SEQ ID NO:4) with water added after the template and before the primers. Lane 14 and 15: 16311A (SEQ ID NO:3) and 16311G (SEQ ID NO:4) with water added before the primers and the primers template. Lane 16 and 17: 16311A (SEQ ID NO:3) and 16311G (SEQ ID NO:4) with water added after the primers and before the template. Lane 18: 100 bp ladder (Promega Corp.).

Figure 8:
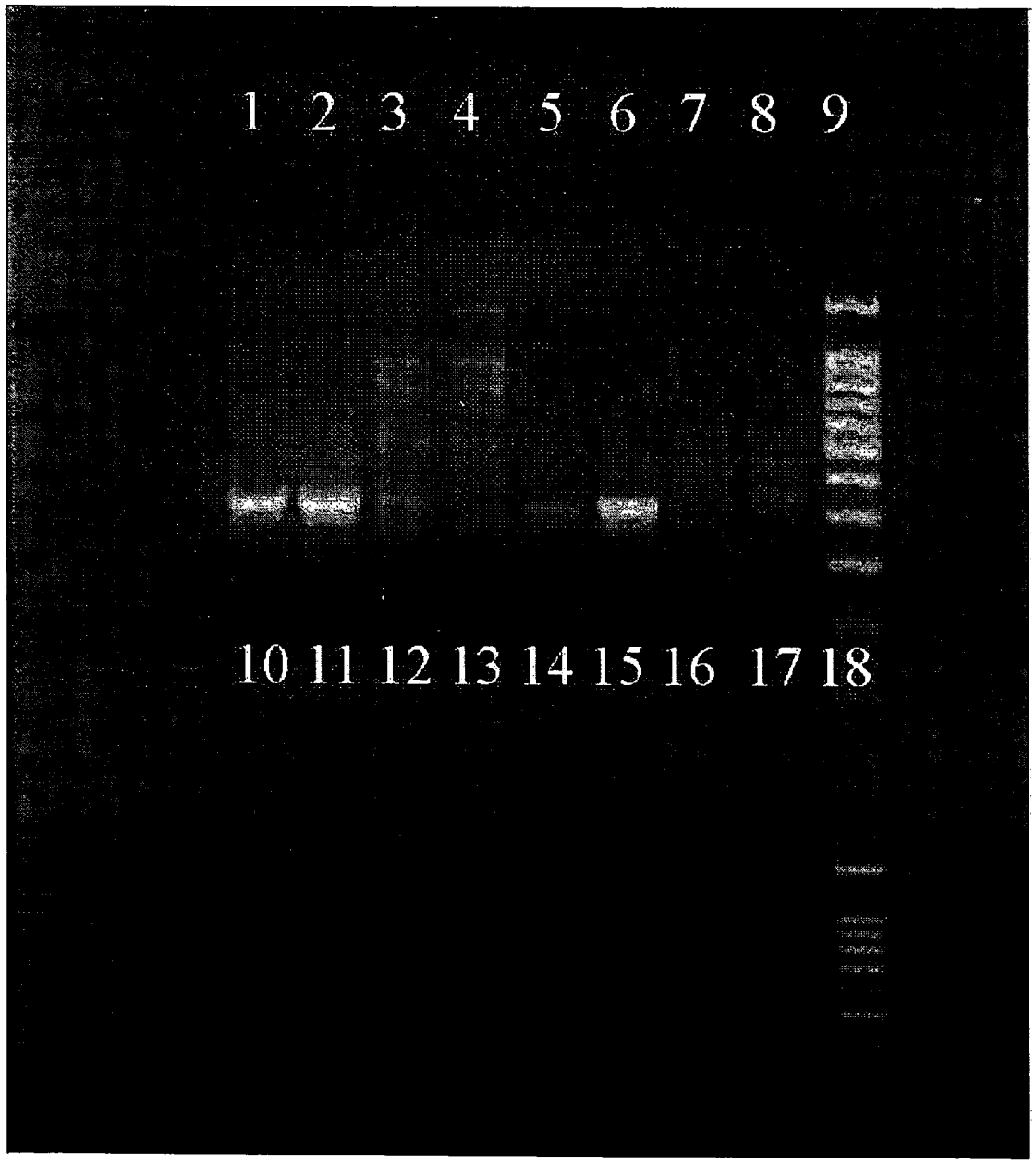

FIG. 8 shows the amplification results on mtDNA in 2% agarose gel stained with ethidium bromide showing the Pfu DNA Polymerase amplification results on mtDNA carrying a T to C transition at position 16311 using primers FW I (SEQ ID NO:1) and either 16311A (SEQ ID NO:3), 16311G (SEQ ID NO 4), 16311T (SEQ ID NO:5) or 16311C (SEQ ID NO:6) at different ethidium bromide concentrations.

Lane 1 through 4: 16311A (SEQ ID NO:3), 16311G (SEQ ID NO:4), 16311T (SEQ ID NO:5) and 16311C (SEQ ID NO:6) without ethidium bromide. Lane 5 through 8: 16311A (SEQ ID NO:3), 16311G (SEQ ID NO:4), 16311T (SEQ ID NO:5) and 16311C (SEQ ID NO:6) with 4.5 µg/ml ethidium bromide. Lane 9: 100 bp ladder (Promega Corp.). Lane 10 through 13: 16311A (SEQ ID NO:3), 16311G (SEQ ID NO:4), 16311T (SEQ ID NO:5) and 16311C (SEQ ID NO:6) with 5.0 µg/ml ethidium bromide. Lane 14 through 17: 16311A (SEQ ID NO:3), 16311G (SEQ ID NO:4), 16311T (SEQ ID NO:5) and 16311C (SEQ ID NO:6) with 5.5 µg/ml ethidium bromide. Lane 18: 100 bp ladder (Promega Corp.).

Figure 9:
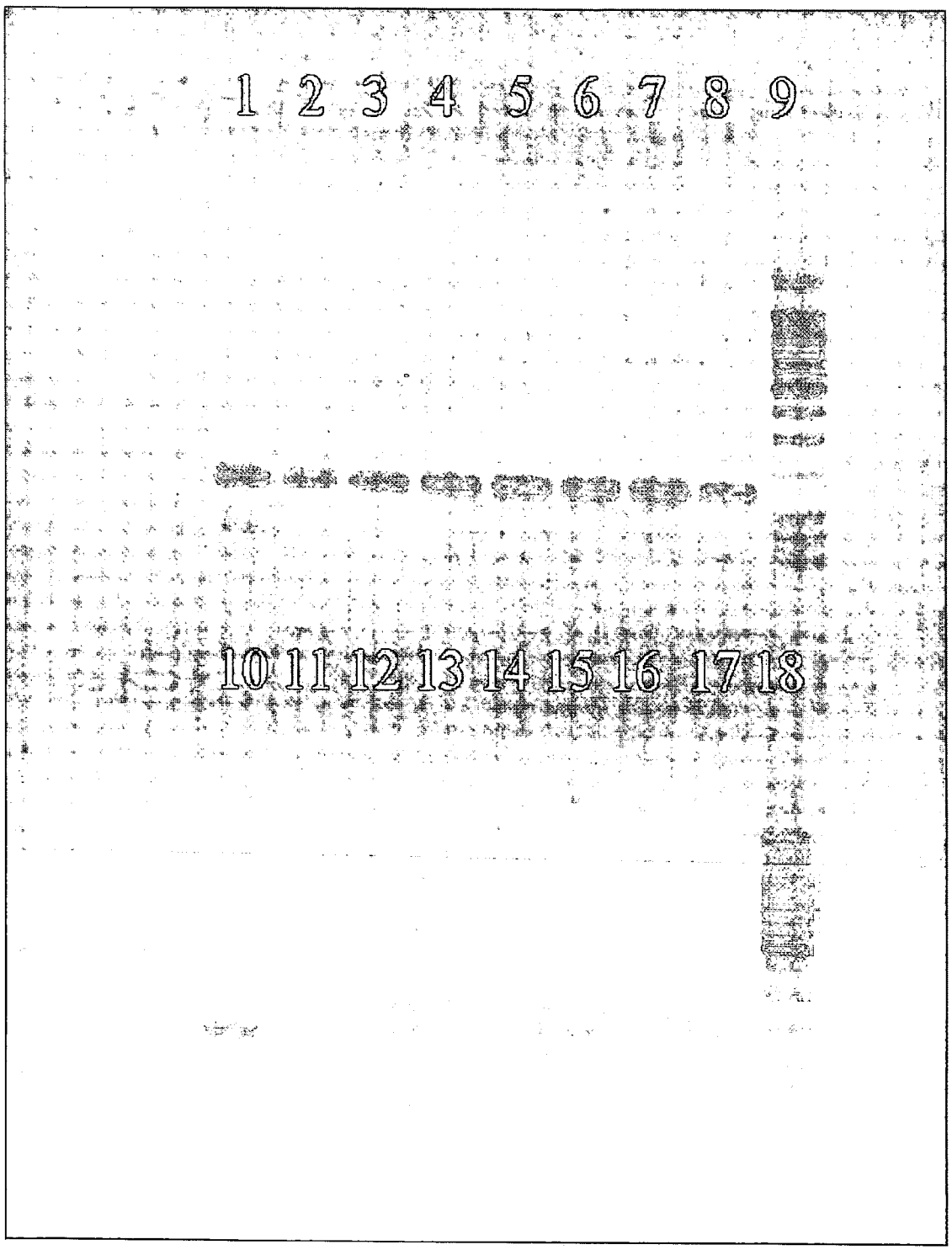

FIG. 9 shows the amplification results on genomic DNA from human patient carrying a C to T transition at position 1785 of the exon 8 of *Homo sapiens* cytochrome b-245 beta polypeptide (CYBB) gene and from an individual control in 2% agarose gel stained with ethidium bromide. DNA samples were amplified with or without ethidium bromide in four separate reactions sharing the upstream primer CYBBBFW (SEQ ID NO:15) and having either of the four alternative downstream primers (CYBB8A (SEQ ID NO:16), CYBBBG (SEQ ID NO:17), CYBB8T (SEQ ID NO:18) and CYBB8C (SEQ ID NO:19).

Lane 1 through 4: CYBB8A (SEQ ID NO:16), CYBB8G (SEQ ID NO:17), CYBB8T (SEQ ID NO:18) and CYBB8C (SEQ ID NO:19) without ethidium bromide, patient DNA. Lane 5 through 8: CYBB8A (SEQ ID NO:16), CYBB8G (SEQ ID NO:17), CYBB8T (SEQ ID NO:18) and CYBB8C (SEQ ID NO:19) without ethidium bromide, control DNA. Lane 9: 100 bp ladder (Promega Corp.). Lane 10 through 13: CYBB8A (SEQ ID NO:16), CYBBBG (SEQ ID NO:17), CYBB8T (SEQ ID NO:18) and CYBB8C (SEQ ID NO:19) with 5.0 µg/ml ethidium bromide, patient DNA. Lane 14 through 17: CYBB8A (SEQ ID NO:16), CYBB8G (SEQ ID NO:17), CYBB8T (SEQ ID NO:18) and CYBB8C (SEQ ID NO:19) with 5.0 µg/ml ethidium bromide, control DNA. Lane 18: 100 bp ladder (Promega Corp.).

FIG. 10-*a*: Shows a scheme of the p3ZIQ24 construct

FIG. 10-*b*: Shows the 2,482 bp amplification product of the lacI gene amplification in 0.7% agarose gel stained with ethidium bromide. DNA samples were amplified with or without ethidium bromide in seven separate reactions using the forward primer OriFw (SEQ ID NO:27) and the reverse primer OriRv (SEQ ID NO:26).

Lanes 1 through 3: without ethidium bromide.

Lanes 4 through, 6: with 2.0 µg/ml ethidium bromide. Lane 7: with 3.0 µg/ml ethidium bromide.

Lane 8: 1 Kb ladder (Promega Corp.).

DESCRIPTION OF THE PREFERRED EMBODIMENTS

Definitions

As use herein, the term intercalating agent" refers a moiety that is able to intercalate between the bases of a nucleic acid molecule.

As use herein, the term transition" is the substitution in DNA or RNA of one purine by another purine, or of one pyrimidine by another pyrimidine.

As use herein, the term "primer" or priming strand" refers either to an oligonucleotide sequence that is added to the reaction extension mixture wherein such oligonucleotide sequence hybridizes with a target sequence on the nucleic acid template, necessary for the beginning of the nucleic acid chain extension reaction or to the growing nucleic acid chain so that whenever a nucleotide is added to the growing chain, this growing chain with the new nucleotide added acts as a primer for the addition of the next nucleotide, and so on.

The present invention provides methods for increasing the fidelity and selectivity of primer or chain extension for polymerases in the presence of an intercalating agent as ethidium bromide when the 3' end of a primer (added primer or growing chain acting as a primer as described above) does not hybridized perfectly with the target sequence. It provides a method for detecting and identifying sequence variation in a nucleic acid by primer extension of polymerases and can be adapted for use as a means for distinguishing or identifying the nucleotide in the target sequence, which is at the site where the mismatch between the primer and the target occurs.

Moreover the present invention also provides a method to increase the fidelity of Taq DNA polymerase by adding ethidium bromide and therefore can be adapted for its use in cloning, expression and all other applications where low error rate may be desired. The fidelity and efficiency improvements may also be well suited for other DNA or RNA polymerase enzymes and for different nucleic acid templates.

The efficiency of primer extension is detected as an indication of the presence and/or identity of the sequence variation in the target. The methods are particularly well suited for detecting and identifying single nucleotide differences between a target sequence of interest, for example a mutant allele of the gene, and a second nucleic acid sequence, for example a wild type allele for the same gene.

Addition of the intercalating agent for example ethidium bromide to an extension reaction mixture or hybridization medium, preferably a PCR reaction mixture improves the selectivity of sequence-specific analyses by decreasing 3'-mismatch in priming and extension of the growing chain. The methods of the invention increase the selectivity of gene variation analyses and suppress the formation of false positive to prevent wrong diagnoses and findings. The method of the invention may be used in any assay that employs an extension step of a target nucleic acid sequence, wherein the 3' end of the added primer does not hybridized perfectly with that target nucleic acid sequence and/or when low error rate products may be desired.

The extension reaction mixture or hybridization media can be any conventional medium known to be suitable for the extension reaction, for example the liquid medium can comprise nucleotide sequence, primers, water, buffer and salts. The extension reaction can be carried out under a wide variety of conditions, having different temperature, electrostatic strength, salt concentration and composition. An expert knows that the concentration of the intercalating agent must be adjusted according the extension conditions and the type of intercalating agent used. In a preferred embodiment, the intercalating agent is ethidium bromide, which is present in the extension reaction mixture in a concentration about 1 µg/ml and 7 µg/ml.

The use of the inventive reaction mixture leads to a clearly improved sensitivity and selectivity of gene polymorphism and gene mutation analyses in animal, bacterial, plants and human genome, preventing wrong diagnoses. It also improves the obtainment of low error rate products necessary for cloning or expression assays. By these means, it is possible to carry out such detections on samples, which previously could not be analyzed in this way. Moreover, the invention leads to a dramatic reduction in the costs of detections, and is rapid and sensitive.

The inventive extension reaction mixture makes possible a distinct increase in the information power of the semi-quantitative and totally quantitative determination of gene variation in tissues and organs in healthy, diseased and medicinally affected state.

In a preferred embodiment, the method of the invention is directed to detecting single nucleotides polymorphisms (SNPs) in a nucleic acid sequence of interest, for example alleles, and to identifying such SNPs or alleles. Such nucleotide sequence variants may be detected directly in a sample to be analyzed during extension and/or amplification of the target sequence.

The inventive methods are based upon the relative inefficiency of primer extension by polymerases enzymes in the presence of an intercalating agent when there are mismatches at the 3' end of a primer hybridized to an otherwise complementary sequence. The method of the invention is useful for detecting mismatches at the 3" end when purine-pyrimidine, purine-purine or pyrimidine-pyrimidine bases mismatches are present.

The difference in the efficiency of polymerase extension (in presence of ethidium bromide) when the primer is hybridized to two different alleles may be used to indicate which allele the target nucleic acid contains. When any one of multiple alleles may be present, multiple primers are employed in the analysis, each with different potential mismatch at or near 3' end. The primer which is most efficient extended provides the identity of the allele, for example the identity of the nucleotide present in the target sequence being analyzed. If the set of primers comprising A, G, C and T at the site of allele to be identified is hybridized to the target sequence and extended, the identity of the allele will be the complement of the nucleotide in the signal primer which was most efficiently extended by the polymerase. The reaction may be performed in monoplex or multiplex format, containing either one or more sets of allelic primers.

The present invention is suitable for SNP assays and for variations that involve mismatches larger than one nucleotide. It may be applied to the currently used methods that rely on primer annealing to distinguish variations in nucleic acid. It may also be useful in the design of defined or random approaches to discover new SNPs.

The application of the invention comprises, above all, a) the pharmacogenomics, especially the discovery of genomic target for drugs candidates, b) detection of nucleotide polymorphisms, especially in molecular diagnosis of disease based on gene mutation analyses and gene polymorphisms, c) molecular diagnosis, especially the screening. and diagnosis of illness relevant genes.

Figure 1:
FIG. 1 shows the amplification results on mtDNA in 2% agarose gel stained with ethidium bromide carrying a T to C transition at position 16311 using primers FW I (SEQ ID NO:1) and either 16311A (SEQ ID NO:3), 16311G (SEQ ID NO:4), 16311T (SEQ ID NO:5) or 16311C (SEQ ID NO:6) at different ethidium bromide concentrations.

The inventors demonstrated that the addition of EtBr improves the specificity of DNA amplification when a 299 bp region of the human mitochondrial D-loop (16,031-16,330) carrying cytosine nucleotide (C) at position 16311 was amplified in four separate PCR reactions sharing the same upstream primer (FW I (SEQ ID NO:1)) and having either of the four 3'-end alternative downstream primers (16311A (SEQ ID NO:3), 16311G (SEQ ID NO:4), 16311T (SEQ ID NO:5) and 16311C (SEQ ID NO:6). Increasing concentrations of ethidium bromide were added to assess the effect on the amplification of the primers carrying different 3' nucleotides. In the absence of ethidium bromide there were ambiguous results. Mismatch primer ●16311A (SEQ ID NO:3) yielded about the same amount of product as the fully homologous primer 16311G (SEQ ID NO:4). There was also some product with mismatch primers 16311T (SEQ ID NO:5) and 16311C (SEQ ID NO:6). The addition of ethidium bromide at concentrations ranging from 4.5 µg/ml to 6.0 µg/ml dramatically diminished the non-specific amplification of all 3' end mismatch primers (16311A (SEQ ID NO:3), 16311C (SEQ ID NO:6) and 16311T (SEQ ID NO:5), although had little effect on the totally complementary one (16311G (SEQ ID NO:4) (FIG. 1). Reciprocally, the same good discrimination was obtained with primer 16311A (SEQ ID NO:3) using mtDNA from a donor carrying Anderson's consensus nucleotide thymine (T) instead of cytosine (C) at position 16311 (12) (FIG. 2). All mtDNA sequences were confirmed by DNA sequencing.

In order to verify if the effect of ethidium bromide was similar in other amplifications the inventors tested other regions of mtDNA. They amplified a 244 bp fragment of region I (16,031-16,275) using upstream primer FW I and downstream primers 16256A (SEQ ID NO:7), 16256G (SEQ ID NO:8), 16256T (SEQ ID NO:9) and 16256C (SEQ ID NO:10) and a 219 bp fragment of region II (16513-162) using upstream primer FW II and downstream primers 143A (SEQ ID NO:11), 143G (SEQ ID NO:12), 143T (SEQ ID NO:13) and 143C (SEQ ID NO:14). Again, the non-specific amplification of mismatch primers was abolished in all cases, regardless of the sequence being amplified (FIG. 3 and FIG. 4). As shown in FIG. 4 some small variations around the optimal concentration of ethidium bromide are observed, which may be due to the different sequences of the primers.

To assess if the primer concentration can affect the selectivity brought about by the addition of ethidium bromide, the inventors tested different amounts of the otherwise hard to distinguish primers 16311A (SEQ ID NO:3) and 16311G (SEQ ID NO:4) in mtDNA carrying cytosine nucleotide (C) at position 16311. No difference in the results was found at the primer amount range tested (0.5, 2.5, 5.0, 50 and 100 pmole) (FIG. 5).

To verify if ethidium bromide was effective with different amounts of template, the inventors added different amounts of mtDNA carrying cytosine nucleotide (C) at position 16311 to the reaction containing either primer 16311A (SEQ ID NO:3) or 16311G (SEQ ID NO:4). The selectivity remained the same regardless of the amount of DNA template used (0.5, 2.0, 10.0, 50 and 500 ng) (FIG. 6).

In order to assess if it was necessary to add the intercalating agent before the primer and the template got together in the reaction, the inventors performed PCR amplifications adding the ethidium bromide before, in between and after the addition of the primer and the template. No differences were observed in any case (FIG. 7).

The inventors tested the effect of ethidium bromide effect when a DNA polymerase carrying a proof-reading, 3'-5' exonuclease activity was used in the reaction instead of Taq DNA Polymerase. The 299 bp region of the mtDNA (16, 031-16,330) carrying cytosine nucleotide (C) at position 16311 was amplified with Pfu DNA Polymerase (Promega) in four separate PCR reactions using primer FW I (SEQ ID NO:1) and the four alternative downstream primers (16311G (SEQ ID NO:4), 16311A (SEQ ID NO:3), 16311C (SEQ ID NO:6) and 16311T (SEQ ID NO:5) at different ethidium bromide concentrations. Surprisingly, despite the editing activity of Pfu DNA Polymerase, it was obtained good specific results at a concentration range of ethidium bromide similar to the one of Taq (FIG. 8). The invention does not require an specific polymerase, any polymerase may be used to obtain the suitable product in an extension reaction.

The inventors tested the discriminatory effect of ethidium bromide on genomic DNA by amplifying a 153 bp region of the exon 8 of *Homo sapiens* cytochrome b-245 beta polypeptide (CYBB) gene (AH011465). CYBB mutations are involved in the X-linked chronic granulomatous disease (CGD) (Jirapongsananuruk, 0., et. Al., *Clin. Immunol*. 104: 73, 2002, cited herein as references). DNA from a male patient having a C to T transition at nucleotide position 1785 and DNA from a male control individual were amplified with or without ethidium bromide in four separate reactions sharing the upstream primer CYBB8FW (SEQ ID NO:15) and having either of the four alternative downstream primers (CYBB8A (SEQ ID NO:16); CYBB8G (SEQ ID NO:17), CYBB8T (SEQ ID NO:18) and CYBB8C (SEQ ID NO:19). Reactions without ethidium bromide gave a non-specific allele amplification product with the four primers in both the patient and the control. On the other hand, reactions containing ethidium bromide at 5 µg/ml yielded a distinct amplification band only with their corresponding homologous primers, CYBBA (SEQ ID NO:16) in the patient and CYBBG (SEQ ID NO:17) in the control (FIG. 9). This result shows that the method of the invention may be used when the template is genomic DNA.

The method of the invention can be used employing any template sequences in an extension reaction, wherein the template is genomic DNA, mitochondrial DNA, synthetic DNA or any nucleotide sequence as RNA sequences when the 3' end of the primer does not hybridized correctly with template target sequence.

In another preferred embodiment, the inventors describe an improvement in fidelity for PCR mixtures containing Taq DNA Polymerase in the presence of an intercalating agent, such as ethidium bromide. The fidelity was measured by using a modification of the lacI PCR mutation assay (Barnes, W. M. (1994) Proc. Natl. Acad. Sci. 91:2216.) described in example 7, that is based on the integrity of the repressor lacI (Farabaugh, P. J. (1978) Nature 274:765) of the Operon Lac. This modified assay, shows that an ethidium bromide concentration as low as 2 µg/ml increases the fidelity of Taq DNA Polymerase by almost two fold.

Throughout this application, various publications are referenced. The disclosures of all of theses publications and those references are hereby incorporated by references into this application in order to more fully describe the state of the art to which this invention pertains.

It should also be understood that the foregoing relates to preferred embodiments of the present invention and that numerous changes may be made therein without departing from the scope of the invention. The invention is further illustrated by the following examples, which are not to be construed in any way as imposing limitation upon the scope thereof. On the contrary, it is to be clearly understood that resort may be had to various other embodiments, modifications, and equivalents thereof, after reading the description herein, may suggest themselves to those skilled in the art without departing from the spirit of the present invention and/or the scope of the appended claims.

EXAMPLES

Example 1

DNA Purification and PCR Amplification

Total DNA was purified from fresh human blood by a salting out procedure using the Wizard® Genomic DNA Purification kit (Promega). Blood was collected in 1.5 ml microtubes containing 100 µl 0.5M EDTA as anticoagulant. Total yield of DNA was about to 10 µg for each sample.

PCR amplifications were performed in a MJ Research PTC-150 thermal cycler in a 25 µl reaction volume containing 10 mM Tris-HCl (pH 9.0), 50 mM KCl, 0.1% Triton® X-100, 1.5 mM MgCl2, 200 uM each deoxy-NTP, 1.5 U Taq DNA Polymerase (Promega Corp.), 25 pmol of upstream primer, 10 pmol of downstream primer and 10 ng of total DNA. Cycling conditions included an initial denaturalization step of 2 min. at 95° C., followed by 36 cycles of 30 sec. at 95° C., 30 sec. at 53° C. and 1 min at 72° C. PCR products were electrophoresed through a 26 agarose gel and visualized with ethidium bromide.

Example 2

Addition of EtBr to the PCR Reaction Mixture to Improve the Specificity of DNA Amplification A 299 bp region of the human mitochondrial D-loop (16,031-16,330) carrying cytosine nucleotide (C) at position 16311 was amplified in four separate PCR reactions sharing the same upstream primer (FWD I Upstream primer 5'-ATG GGG AAG CAG ATT TGG GT-3' (SEQ ID NO:1) and having either of the four 3'-end alternative downstream primers (16311A (SEQ ID NO:3) downstream primer 5'-ACG GTA AAT GGC TTT ATG TA-3', 16311G (SEQ ID NO:4) downstream primer 5'-ACG GTA AAT GGC TTT ATG TG-3', 16311T (SEQ ID NO:5) downstream primer 5'-ACG GTA AAT GGC TTT ATG TT-3', 16311C (SEQ ID NO:6) downstream primer 5'-ACG GTA AAT GGC TTT ATG TC-3'). The PCR was carried out as in the example 1, except of increasing concentrations of ethidium bromide were added to assess the effect on the amplification of the primers carrying different 3' nucleotides. The increasing concentrations of ethidium bromide were from 4.5 to 6.0 µg/ml.

In order to verify if the effect of ethidium bromide was similar in other amplifications, we tested other regions of mtDNA. We amplified a 244 bp fragment of region I (16,031-16,275) using upstream primer FW I (showed above) and downstream primers (16256A (SEQ ID NO:7) downstream primer 5'-TCC TAG TGG GTG AGG GGT GA-3', 16256G (SEQ ID NO:8) downstream primer 5'-TCC TAG TGG GTG AGG GGT GG-3', 16256T (SEQ ID NO:9) downstream primer 5'-TCC TAG TGG GTG AGG GGT GT-3' and 16256C (SEQ ID NO:10) downstream primer 5'-TCC TAG TGG GTG AGG GGT GC-3'); and a 219 bp fragment of region II (16513-162) using upstream primer FW I I (FWD I I Upstream primer 5'-TCA GGG TCA TAA AGC CTA AA-3' (SEQ ID NO:2) and downstream primers 143A (SEQ ID NO:11) downstream primer 5'-GAT AAA TAA TAG GAT GAG GA-3', 143G (SEQ ID NO:12) downstream primer 5'-GAT AAA TAA TAG GAT GAG GG-3', 143T (SEQ ID NO:13) downstream primer 5'-GAT AAA TAA TAG GAT GAG GT-3', 143C (SEQ ID NO:14) downstream primer 5'-GAT AAA TAA TAG GAT GAG GC-3').

The PCR was carried out as in the example 1, except of increasing concentrations of ethidium bromide were added to assess the effect on the amplification of the primers carrying different 3' nucleotides in different regions of mtDNA. The increasing concentrations of ethidium bromide were from 4.5 to 6.0 µg/ml in the amplification of the 244 bp fragment and from 5.0 to 6.5 µg/ml in the amplification of the 219 bp fragment.

Example 3

The Effect of Primer Concentration and Amount of Template in the Methods of the Invention To assess if the primer concentration can affect the selectivity brought about by the addition of ethidium bromide, was tested different amounts of the otherwise hard to distinguish primers 16311A (SEQ ID NO:3) and 16311G (SEQ ID NO:4) (sequence showed above) in mtDNA carrying cytosine nucleotide (C) at position 16311. The PCR was carried out as in the example 1. Ethidium bromide concentration in the PCR reaction mixture was 5.0 µg/ml and primers amounts were from 0.5 to 100 pmole.

To verify if ethidium bromide was equally effective with different amounts of template, were added different amounts of mtDNA carrying cytosine nucleotide (C) at position 16311 to the reaction containing either primer 16311A (SEQ ID NO:3) or 16311G (SEQ ID NO:4).

The PCR was carried out as in the example 1. Ethidium bromide concentration in the PCR reaction mixture was 5.0 µg/ml, template amount was from 0.5 ng to 500 ng.

Example 4

Adding Ethidium Bromide at Different Time

In order to assess if it was necessary to add the intercalating agent before the primer and the template got together in the reaction, we performed PCR amplifications adding the ethidium bromide before, in between and after the addition of the primer and the template.

The PCR was carried out as in the example 1 adding 5.0 µg/ml of ethidium bromide before, between and after the primers and template.

Example 5

PCR Amplification Using Proofreading Enzyme Instead Taq DNA Polymerase

PCR Reaction Mixture and Conditions:

Proofreading amplifications were performed with 0.6 U of Pfu DNA Polymerase (Promega Corp.) in 20 mM Tris-HCl (pH 8.8), 10 mM KCl, 0.1% Triton® X-100, 2 mM MgSO4, 10 nM (NH4)SO4, 0.1 mg/ml BSA, 200 uM each deoxy-NTP, 25 pmol of upstream primer, 10 pmol of downstream primer and 10 ng of total DNA under the same cycling conditions described in the example 1, except of increasing concentrations of ethidium bromide (from 4.5 to 5.5 µg/ml) were added. PCR products were electrophoresed through a 2% agarose gel and visualised with ethidium bromide.

Primers and Templates:

The 299 bp region of the mtDNA (16,031-16,330) carrying cytosine nucleotide (C) at position 16311 was amplified with Pfu DNA Polymerase (Promega) in four separate PCR reactions using primer FW I (sequence showed above) and the four alternative downstream primers 16311G (SEQ ID NO:4), 16311A (SEQ ID NO:3), 16311C (SEQ ID NO:6) and 16311T (SEQ ID NO:5) (sequences showed above).

Example 6

Detection of a Single-Base Mutation in Exon 8 of Homo sapiens Cytochrome b-245 Beta Polypeptide (CYBB) Gene Using the Method of the Invention The PCR was carried out as in the example 1, adding 10 pmole of both primers and 5.0/g/ml of ethidium bromide. The sequence of the primers was:

CYBB8FW Upstream primer 5'-CTC CCT CTG AAT ATT TTG TTA TC-3' (SEQ ID NO:15)

CYBB8A Downstream primer 5'-GAC CAC CTT CTG TTG AGA TCA-3' (SEQ ID NO:16)

CYBB8G Downstream primer 5'-GAC CAC CTT CTG TTG AGA TCG-3' (SEQ ID NO:17)

CYBB8T Downstream primer 5'-GAC CAC CTT CTG TTG AGA TCT-3' (SEQ ID NO:18)

CYBB8C Downstream primer 5'-GAC CAC CTT CTG TTG AGA TCC-3' (SEQ ID NO:19)

Example 7

Fidelity of Taq DNA Polymerase is Enhanced by Ethidium Bromide

It has been previously demonstrated in the present application than the intercalating agent ethidium bromide helps to prevent the incorporation of nucleotides in the presence of a primer carrying a mismatch at the 3' end. If this enhanced primer selectivity occurred in every single nucleotide addition during the polymerization reaction it would then render a more accurate final product, regardless of the existence of any editing function. In order to demonstrate this, the lacI test was performed as follow:

Overview of the lacI Test

A 2.5 kb fragment encoding orilac$^q$IOZ' was PCR amplified with primers containing 5' NsiI and NdeI restriction sites and digested with these two restriction enzymes. It was then ligated into a previously NsiI/NdeI-digested 1.3 kb fragment that contains the 13-lactamase sequence. The resulting plasmid was transformed into E. coli JM109 competent cells and plated on agar with ampicilin (100 µg/ml) plus X-gal (80 µg/ml). Blue and white colonies were counted.

Construction of the p3ZIQ24 Template

The truncated lacI gene (SEQ ID NO:20) of the pGEM®-3Z vector (Promega Corp. SEQ ID NO:21) was substituted by a functional copy of the lacI$^q$ repressor gene derived from the E. coli strain HB101. The 1,389 bp lacI$^q$ fragment was obtained by amplifying the lacI region of HB101 with primers lacIFw (SEQ ID NO:23) and lacIRv (SEQ ID NO:22). The latter carries a C to T transition at the position −35 of the gene, conferring the strong lacI$^q$ promoter genotype to the construct (Calos, P. M. (1978) Nature 274:762). The lacI$^q$ fragment was cloned blunt on a Pst I-digested pGem 3Z plasmid lacking the 379 bp Pst I-Pst I region. The new plasmid of 3,753 bp (FIG. 10-a), named p3ZIQ24, was used as the template for the PCR fidelity assays.

Polymerase Chain Reactions

PCR amplifications (Mullis, K. B. (1990) Ann. Biol. Clin. 0.48:579) were performed in a MJ Research PTC-150 thermal cycler in a 25 gl reaction volume containing 10 mM Tris-HCl (pH 9.0), 50 mM KCl, 0.1% Triton® X-100, 1.5 mM MgCl$_2$, 200 µM each deoxy-NTP, 1.2 U Taq DNA Polymerase (Promega Corp.) or Tli DNA Poymerase (Promega Corp.), 100 pmole of each primer and 0.1 ng of p3ZIQ24 as template. Cycling conditions included an initial denaturalization step of 4 min at 94° C., followed by 36 cycles of 30 sec. at 94° C., 30 sec. at 50° C. and 4 min. at 72° C. PCR products were electrophoresed through a 0.7% TAE-agarose gel and visualized under UV with ethidium bromide. The input and output DNA was quantified by gel densitometry with the AlphaEase® software (AlphaInnotech Inc.).

Cloning of the PCR Products

A 2482 bp lacI$^q$ fragment carrying the origin region of p3ZIg24 was generated by PCR with primers OriFw (SEQ ID NO:27) and OriRv (SEQ ID NO:26). A 1270 bp fragment having the beta-lactamase region of p3ZIg24 was obtained with primers AmpRv (SEQ ID NO:24) and AmpFw (SEQ ID NO:25). Since primers OriRv and AmpFw carry a NsiI restriction site and primers OriFw and AmpRv a NdeI site both fragments were digested with the restriction enzymes NsiI and NdeI to create cohesive ends. They were then purified with Wizard® SV Gel and PCR Clean Up (Promega) and ligated in a 1:1 ratio overnight at 18° C. The resulting plasmids were transformed in triplicates in E. coli JM109 competent cells (Sambrook, J. Fritsch, E. F. and Maniatis, T. (1989). Molecular Cloning A Laboratory Manual. Second edition. Cold Spring Harbor Laboratory Press 1.74) and plated on LB-Amp X-Gal plates.

LacI Based Assay

After overnight incubation at 37° C. blue and white colonies were counted. The error rate (f) was calculated according to the following formula (Keohavong, P. and Thiliy, W. G. (1989) Proc. Natl. Acad. Sci. 86:9253):

$$f=-\ln F/d \times b$$

where F is the fraction of white colonies over the total, d is the number of duplications (2d=output DNA/input DNA) and b is the effective target site, which is 349 bp for lacI (Provost, G. S., Kretz, P. L., Hamner, R. T., Matthews, C. D., Rogers, B. J., Lundberg, K. S., Dycaico, M. J. and Short, J. M. (1993) *Mut. Research* 288:133).

Results

Table 1 illustrates that the ethidium bromide treatment improves the fidelity performance of Taq DNA polymerase. Using a 2 pg/ml concentration of ethidium bromide the error rate is $1.3 \times 10^{-5}$, comparing to $2.1 \times 10^{-5}$ without treatment. The error rate determined for Taq DNA polymerase agrees with the figures published in the literature (Lundberg, K. S., Shoemaker, D. D., Adams, M. W., Short, J. M., Sorge, J. A. and Mathur, E. J. (1991) *Gene* 108:1). The error rate with ethidium bromide was reduced by almost a half. FIG. 10-b shows that the yield of the 2,482 bp PCR product is somewhat lower in the presence of the intercalating agent, a feature common to many high fidelity reactions. According to this and as it was mentioned previously in this present application nucleic acid sequences may be accurate amplified without the use of any other reagent than a correct amount of ethidium bromide.

TABLE 1

|  | P3ZIQ24 (ng) | Product (ng) | d | N° Blue Colonies | N° White Colonies | N° Total Colonies | % lacI- | F |
|---|---|---|---|---|---|---|---|---|
| EtBr 0 µg/ml |  | 3000 | 14.9 | 65 | 440 | 505 | 12.87 |  |
| EtBr 0 µg/ml | 0.1 | 3000 | 14.9 | 52 | 499 | 551 | 9.44 |  |
| EtBr 0 µg/ml | 0.1 | 3000 | 14.9 | 47 | 447 | 494 | 9.51 |  |
| TOTAL |  |  |  | 164 | 1386 | 1550 | 10.58 | $2.1 \times 10^{-5}$ |
| EtBr 2 µg/ml | 0.1 | 50 | 9 | 23 | 630 | 653 | 3.52 |  |
| EtBr 2 µg/ml | 0.1 | 50 | 9 | 32 | 748 | 780 | 4.10 |  |
| EtBr 2 µg/ml | 0.1 | 50 | 9 | 26 | 520 | 546 | 4.76 |  |
| TOTAL |  |  |  | 81 | 1898 | 1979 | 4.09 | $1.3 \times 10^{-5}$ |

While preferred embodiments of the present invention have been illustrated and described, it will be obvious to those skilled in the art that various changes and modifications may be made therein without departing from the scope of the invention as defined in the appended claims.

We claim:

1. A method for increasing the selectivity or fidelity of extension of a nucleic acid sample by polymerase enzymes utilizing a primer where the 3' end of a primer does not hybridize perfectly with the target, wherein the primer is
   i) an added primer or
   ii) a growing nucleic acid chain that is being polymerized, the growing nucleic acid chain acting as a primer for the addition of the next nucleotide of the sequence, the method comprising the steps of:
   a) obtaining a nucleic acid sample;
   b) hybridizing the nucleic acid sample to a primer;
   c) providing a reaction extension mixture comprising a polymerizing enzyme and an ethidium bromide present in an amount of from about 4 to about 7 µg/ml;
   d) subjecting the hybridized nucleic acid sample to an extension reaction by extending the primer with a polymerizing enzyme, and blocking the primer in the extension reaction of step c) by polymerizing enzymes where the 3' end of a primer does not hybridize perfectly with the target, thereby increasing the selectivity of single nucleotide mutation or gene analyses by suppressing false positive results, and e) detecting the presence of extension products or amplified products.

2. The method of claim 1, where the extension reaction during which a primer is extended with a polymerizing enzyme in step (d) is the extension reaction step in a PCR procedure and the extension reaction medium is a PCR reaction mixture and step (e) the detection of amplified products.

3. The method of claim 1, where step (b) comprises hybridizing the nucleic acid sample to primers in a monoplex or multiplex format containing one or more sets of allelic primers.

4. The method of claim 2, wherein one or more primers are employed in the PCR.

5. The method of claim 2, wherein the polymerizing enzyme is DNA or RNA polymerases, with or without editing activity; native or recombinant enzyme; thermostable or non-thermostable enzyme; complete enzyme or some active fragment.

6. The method of claim 2, wherein the polymerizing enzyme is DNA or RNA polymerases, with or without editing activity.

7. The method of claim 2, wherein the polymerizing enzyme is selected from the group consisting of thermostable enzymes.

8. A method for enhancing the fidelity and selectivity of polymerase chain reactions comprising the steps of:
   (a) obtaining a nucleic acid sample;
   (b) hybridizing said nucleic acid sample to a primer;
   (c) subjecting said hybridized nucleic acid sample to an extension reaction by extending the primer with a polymerizing enzyme, wherein the extension reaction mixture contains an ethidium bromide in an amount of from about 4 to about 7 μg/ml; and
   (d) detecting the presence of extension products.

9. The method of claim 8, wherein the extension reaction during which a primer is extended with a polymerizing enzyme in step (c) is the extension reaction in a PCR procedure and the extension reaction medium is a PCR reaction mixture, wherein said PCR reaction mixture contains said ethidium bromide and, step (d) is the detection of amplified products.

10. In a method of increasing the selectivity and fidelity of primer extension by polymerase in a reaction mixture comprising a target nucleic acid, primers and a polymerase, where the 3' end of the primer does not hybridize perfectly with the target sequence, the improvement comprising adding to the reaction mixture from about 4 to about 7 μg/ml of the reaction mixture of an ethidium bromide.

11. The method of claim 10, where the primer extension occurs in the extension reaction steps of a PCR procedure, the extension reaction mixture is a PCR reaction mixture, further comprising detecting the amplified products.

12. In a method of amplifying a nucleic acid sample with increased fidelity by polymerase enzymes in a polymerase chain reaction utilizing a primer consisting of a growing nucleic acid chain that is being polymerized, the growing nucleic acid chain acting as a primer for the addition of the next nucleotide of the sequence, the improvement comprising adding to the reaction mixture ethidium bromide in an amount of from about 4 to about 7 μg/ml of the reaction mixture.

13. A method for increasing the selectivity or fidelity of extension of a nucleic acid sample by polymerase enzymes utilizing a primer where the 3' end of a primer does not hybridize perfectly with the target, wherein the primer is
   i) an added primer or
   ii) a growing nucleic acid chain that is being polymerized, the growing nucleic acid chain acting as a primer for the addition of the next nucleotide of the sequence,
the method comprising the steps of:
   a) obtaining a nucleic acid sample;
   b) hybridizing the nucleic acid sample to a primer;
   c) providing a reaction extension mixture comprising a polymerizing enzyme and an ethidium bromide present in an amount of from about 4 to about 7 μg/ml
   d) subjecting the hybridized nucleic acid sample to an extension reaction by extending the primer with a polymerizing enzyme, and blocking the primer in the extension reaction of step c) by polymerizing enzymes where the 3' end of a primer does not hybridize perfectly with the target, thereby increasing the selectivity of single nucleotide mutation or gene analyses by suppressing false positive results, and
   e) detecting the presence of extension products or amplified products.

* * * * *

SEQUENCE LISTING

<160> NUMBER OF SEQ ID NOS: 27

<210> SEQ ID NO 1
<211> LENGTH: 20
<212> TYPE: DNA
<213> ORGANISM: Artificial
<220> FEATURE:
<223> OTHER INFORMATION: Human mitochondrial D-loop (16,031-16,330, carrying cytosine nucleotide (C) at position 16311) upstream primer

<400> SEQUENCE: 1
atggggaagc agatttgggt                                                  20

<210> SEQ ID NO 2
<211> LENGTH: 20
<212> TYPE: DNA
<213> ORGANISM: Artificial
<220> FEATURE:
<223> OTHER INFORMATION: Human mtDNA (219 bp fragment of region II, 16513-162) upstream primer

<400> SEQUENCE: 2

```
tcagggtcat aaagcctaaa                                               20

<210> SEQ ID NO 3
<211> LENGTH: 20
<212> TYPE: DNA
<213> ORGANISM: Artificial
<220> FEATURE:
<223> OTHER INFORMATION: Human mitochondrial D-loop (16,031-16,330,
      carriying adenosine nucleotide (A) al position 16311) downstream
      primer

<400> SEQUENCE: 3
acggtaaatg gctttatgta                                               20

<210> SEQ ID NO 4
<211> LENGTH: 20
<212> TYPE: DNA
<213> ORGANISM: Artificial
<220> FEATURE:
<223> OTHER INFORMATION: Human mitochondrial D-loop (16,031-16,330,
      carriying guanosine nucleotide (G) al position 16311) downstream
      primer

<400> SEQUENCE: 4
acggtaaatg gctttatgtg                                               20

<210> SEQ ID NO 5
<211> LENGTH: 20
<212> TYPE: DNA
<213> ORGANISM: Artificial
<220> FEATURE:
<223> OTHER INFORMATION: Human mitochondrial D-loop (16,031-16,330,
      carriying thymidine nucleotide (T) at position 16311) downstream
      primer

<400> SEQUENCE: 5
acggtaaatg gctttatgtt                                               20

<210> SEQ ID NO 6
<211> LENGTH: 20
<212> TYPE: DNA
<213> ORGANISM: Artificial
<220> FEATURE:
<223> OTHER INFORMATION: Human mitochondrial D-loop (16,031-16,330,
      carriying cytosine nucleotide (C) at position 16311) downstream
      primer

<400> SEQUENCE: 6
acggtaaatg gctttatgtc                                               20

<210> SEQ ID NO 7
<211> LENGTH: 20
<212> TYPE: DNA
<213> ORGANISM: Artificial
<220> FEATURE:
<223> OTHER INFORMATION: Human mtDNA (244 bp fragment of region I, 16,
      031-16,275, carrying adenosine nucleotide (A) al position 16256)
      downstream primer

<400> SEQUENCE: 7
tcctagtggg tgagggtga                                                20

<210> SEQ ID NO 8
<211> LENGTH: 20
<212> TYPE: DNA
<213> ORGANISM: Artificial
<220> FEATURE:
```

<223> OTHER INFORMATION: Human mtDNA (244 bp fragment of region I, 16,
031-16,275, carrying guanosine nucleotide (G) at position 16256)
downstream primer

<400> SEQUENCE: 8
tcctagtggg tgagggtgg                                                    20

<210> SEQ ID NO 9
<211> LENGTH: 20
<212> TYPE: DNA
<213> ORGANISM: Artificial
<220> FEATURE:
<223> OTHER INFORMATION: Human mtDNA (244 bp fragment of region I, 16,
031-16,275, carrying thyrosine nucleotide (T) at position 16256)
downstream primer

<400> SEQUENCE: 9
tcctagtggg tgagggtgt                                                    20

<210> SEQ ID NO 10
<211> LENGTH: 20
<212> TYPE: DNA
<213> ORGANISM: Artificial
<220> FEATURE:
<223> OTHER INFORMATION: Human mtDNA (244 bp fragment of region I, 16,
031-16,275, carrying cytosine nucleotide (C) at position 16256)
downstream primer

<400> SEQUENCE: 10
tcctagtggg tgagggtgc                                                    20

<210> SEQ ID NO 11
<211> LENGTH: 20
<212> TYPE: DNA
<213> ORGANISM: Artificial
<220> FEATURE:
<223> OTHER INFORMATION: Human mtDNA downstream primer

<400> SEQUENCE: 11
gataaataat aggatgagga                                                   20

<210> SEQ ID NO 12
<211> LENGTH: 20
<212> TYPE: DNA
<213> ORGANISM: Artificial
<220> FEATURE:
<223> OTHER INFORMATION: Human mtDNA downstream primer

<400> SEQUENCE: 12
gataaataat aggatgaggg                                                   20

<210> SEQ ID NO 13
<211> LENGTH: 20
<212> TYPE: DNA
<213> ORGANISM: Artificial
<220> FEATURE:
<223> OTHER INFORMATION: Human mtDNA downstream primer

<400> SEQUENCE: 13
gataaataat aggatgaggt                                                   20

<210> SEQ ID NO 14
<211> LENGTH: 20
<212> TYPE: DNA
<213> ORGANISM: Artificial
<220> FEATURE:
<223> OTHER INFORMATION: Human mtDNA downstream primer

<400> SEQUENCE: 14
gataaataat aggatgaggc                                                 20

<210> SEQ ID NO 15
<211> LENGTH: 23
<212> TYPE: DNA
<213> ORGANISM: Artificial
<220> FEATURE:
<223> OTHER INFORMATION: Homo sapiens Cytochrome b-245 beta upstream
      primer

<400> SEQUENCE: 15
ctccctctga atattttgtt atc                                             23

<210> SEQ ID NO 16
<211> LENGTH: 21
<212> TYPE: DNA
<213> ORGANISM: Artificial
<220> FEATURE:
<223> OTHER INFORMATION: Homo sapiens Cytochrome b-245 beta downstream
      primer

<400> SEQUENCE: 16
gaccaccttc tgttgagatc a                                               21

<210> SEQ ID NO 17
<211> LENGTH: 21
<212> TYPE: DNA
<213> ORGANISM: Artificial
<220> FEATURE:
<223> OTHER INFORMATION: Homo sapiens Cytochrome b-245 beta downstream
      primer

<400> SEQUENCE: 17
gaccaccttc tgttgagatc g                                               21

<210> SEQ ID NO 18
<211> LENGTH: 21
<212> TYPE: DNA
<213> ORGANISM: Artificial
<220> FEATURE:
<223> OTHER INFORMATION: Homo sapiens Cytochrome b-245 beta downstream
      primer

<400> SEQUENCE: 18
gaccaccttc tgttgagatc t                                               21

<210> SEQ ID NO 19
<211> LENGTH: 21
<212> TYPE: DNA
<213> ORGANISM: Artificial
<220> FEATURE:
<223> OTHER INFORMATION: Homo sapiens Cytochrome b-245 beta downstream
      primer

<400> SEQUENCE: 19
gaccaccttc tgttgagatc c                                               21

<210> SEQ ID NO 20
<211> LENGTH: 1390
<212> TYPE: DNA
<213> ORGANISM: Escherichia coli

<400> SEQUENCE: 20
ctggcgaaag ggggatgtgc tgcaaggcga ttaagttggg taacgccagg gttttcccag     60

-continued

```
tcacgacgtt gtaaaacgac ggccagtgaa tccgtaatca tggtcatagc tgtttcctgt        120
gtgaaattgt tatccgctca caattccaca acatacga gccggaagca taaagtgtaa         180
agcctggggt gcctaatgag tgagctaact cacattaatt gcgttgcgct cactgcccgc       240
tttccagtcg ggaaacctgt cgtgccagct gcattaatga atcggccaac gcgcggggag       300
aggcggtttg cgtattgggc gccagggtgg ttttcttttt caccagtgag acgggcaaca      360
gctgattgcc cttcaccgcc tggccctgag agagttgcag caagcggtcc acgctggttt      420
gccccagcag cgcgaaaatcc tgtttgatgg tggttaacgg cgggatataa catgagctgt     480
cttcggtatc gtcgtatccc actaccgaga tatccgcacc aacgcgcagc ccggactcgg      540
taatggcgcg cattgcgccc agcgccatct gatcgttggc aaccagcatc gcagtgggaa      600
cgatgccctc attcagcatt tgcatggttt gttgaaaacc ggacatggca ctccagtcgc      660
cttcccgttc cgctatcggc tgaatttgat tgcgagtgag atatttatgc cagccagcca     720
gacgcagacg cgccgagaca gaacttaatg ggcccgctaa cagcgcgatt tgctggtgac      780
ccaatgcgac cagatgctcc acgcccagtc gcgtaccgtc ttcatgggag aaaataatac     840
tgttgatggg tgtctggtca gagacatcaa gaaataacgc cggaacatta gtgcaggcag     900
cttccacagc aatggcatcc tggtcatcca gcggatagtt aatgatcagc ccactgacgc     960
gttgcgcgag aagattgtgc accgccgctt tacaggcttc gacgccgctt cgttctacca     1020
tcgacaccac cacgctggca cccagttgat cggcgcgaga tttaatcgcc gcgacaattt    1080
gcgacggcgc gtgcagggcc agactggagg tggcaacgcc aatcagcaac gactgtttgc      1140
ccgccagttg ttgtgccacg cggttgggaa tgtaattcag ctccgccatc gccgcttcca    1200
cttttttccg cgttttcgca gaaacgtggc tggcctggtt caccacgcgg gaaacggtct     1260
gataagagac accggcatac tctgcgacat cgtataacgt tactggtttc acattcacca     1320
ccctgaattg actctcttcc gggcgctatc atgccatacc gcgaaaggtt ttgcgccatt    1380
cgatggtgtc                                                             1390
```

<210> SEQ ID NO 21
<211> LENGTH: 2743
<212> TYPE: DNA
<213> ORGANISM: Artificial
<220> FEATURE:
<223> OTHER INFORMATION: pGEM*-3Zvector secuence (Promega Corp.)

<400> SEQUENCE: 21

```
gggcgaattc gagctcggta cccggggatc ctctagagtc gacctgcagg catgcaagct       60
tgagtattct atagtgtcac ctaaatagct tggcgtaatc atggtcatag ctgtttcctg      120
tgtgaaattg ttatccgctc acaattccac aacatacg agccggaagc ataaagtgta        180
aagcctgggg tgcctaatga gtgagctaac tcacattaat tgcgttgcgc tcactgcccg     240
cttttcagtc gggaaacctg tcgtgccagc tgcattaatg aatcggccaa cgcgcgggga    300
gaggcggttt gcgtattggg cgctcttccg cttcctcgct cactgactcg ctgcgctcgg     360
tcgttcggct gcggcgagcg gtatcagctc actcaaaggc ggtaatacgg ttatccacag    420
aatcagggga taacgcagga agaacatgt gagcaaaagg ccagcaaaag gccaggaacc    480
gtaaaaaggc cgcgttgctg cgttttttcc ataggctccg cccccctgac gagcatcaca     540
aaaatcgacg ctcaagtcag aggtggcgaa acccgacagg actataaaga taccaggcgt    600
ttccccctgg aagctccctc gtgcgctctc ctgttccgac cctgccgctt accggatacc    660
```

```
tgtccgcctt tctcccttcg ggaagcgtgg cgctttctca tagctcacgc tgtaggtatc    720
tcagttcggt gtaggtcgtt cgctccaagc tgggctgtgt gcacgaaccc cccgttcagc    780
ccgaccgctg cgccttatcc ggtaactatc gtcttgagtc caacccggta agacacgact    840
tatcgccact ggcagcagcc actggtaaca ggattagcag agcgaggtat gtaggcggtg    900
ctacagagtt cttgaagtgg tggcctaact acggctacac tagaagaaca gtatttggta    960
tctgcgctct gctgaagcca gttaccttcg gaaaagagt tggtagctct tgatccggca    1020
aacaaaccac cgctggtagc ggtggttttt ttgtttgcaa gcagcagatt acgcgcagaa    1080
aaaaggatc tcaagaagat cctttgatct tttctacggg gtctgacgct cagtggaacg    1140
aaaactcacg ttaagggatt ttggtcatga gattatcaaa aaggatcttc acctagatcc    1200
ttttaaatta aaaatgaagt tttaaatcaa tctaaagtat atatgagtaa acttggtctg    1260
acagttacca atgcttaatc agtgaggcac ctatctcagc gatctgtcta tttcgttcat    1320
ccatagttgc ctgactcccc gtcgtgtaga taactacgat acgggagggc ttaccatctg    1380
gccccagtgc tgcaatgata ccgcgagacc cacgctcacc ggctccagat ttatcagcaa    1440
taaaccagcc agccggaagg gccgagcgca gaagtggtcc tgcaacttta tccgcctcca    1500
tccagtctat taattgttgc cgggaagcta gagtaagtag ttcgccagtt aatagtttgc    1560
gcaacgttgt tgccattgct acaggcatcg tggtgtcacg ctcgtcgttt ggtatggctt    1620
cattcagctc cggttcccaa cgatcaaggc gagttacatg atcccccatg ttgtgcaaaa    1680
aagcggttag ctccttcggt cctccgatcg ttgtcagaag taagttggcc gcagtgttat    1740
cactcatggt tatggcagca ctgcataatt ctcttactgt catgccatcc gtaagatgct    1800
tttctgtgac tggtgagtac tcaaccaagt cattctgaga atagtgtatg cggcgaccga    1860
gttgctcttg cccggcgtca atacgggata ataccgcgcc acatagcaga actttaaaag    1920
tgctcatcat tggaaaacgt tcttcggggc gaaaactctc aaggatctta ccgctgttga    1980
gatccagttc gatgtaaccc actcgtgcac ccaactgatc ttcagcatct tttactttca    2040
ccagcgtttc tgggtgagca aaaacaggaa ggcaaaatgc cgcaaaaaag gaataagggg    2100
cgacacggaa atgttgaata ctcatactct tcctttttca atattattga agcatttatc    2160
agggttattg tctcatgagc ggatacatat ttgaatgtat ttagaaaaat aaacaaatag    2220
gggttccgcg cacatttccc cgaaaagtgc cacctgacgt ctaagaaacc attattatca    2280
tgacattaac ctataaaaat aggcgtatca cgaggccctt tcgtctcgcg cgtttcggtg    2340
atgacggtga aaacctctga cacatgcagc tcccggagac ggtcacagct tgtctgtaag    2400
cggatgccgg gagcagacaa gcccgtcagg gcgcgtcagc gggtgttggc gggtgtcggg    2460
gctggcttaa ctatgcggca tcagagcaga ttgtactgag agtgcaccat atgcggtgtg    2520
aaataccgca cagatgcgta aggagaaaat accgcatcag gcgccattcg ccattcaggc    2580
tgcgcaactg ttgggaaggg cgatcggtgc gggcctcttc gctattacgc cagctggcga    2640
aagggggatg tgctgcaagg cgattaagtt gggtaacgcc agggttttcc cagtcacgac    2700
gttgtaaaac gacggccagt gaattgtaat acgactcact ata                      2743
```

<210> SEQ ID NO 22
<211> LENGTH: 20
<212> TYPE: DNA
<213> ORGANISM: Artificial
<220> FEATURE:
<223> OTHER INFORMATION: Reverse primer used in LacI based Assay

<400> SEQUENCE: 22

```
gacaccatcg aatggtgcaa                                                    20

<210> SEQ ID NO 23
<211> LENGTH: 21
<212> TYPE: DNA
<213> ORGANISM: Artificial
<220> FEATURE:
<223> OTHER INFORMATION: Forward  primer used in LacI based Assay

<400> SEQUENCE: 23
ctggcgaaag ggggatgtgc t                                                  21

<210> SEQ ID NO 24
<211> LENGTH: 20
<212> TYPE: DNA
<213> ORGANISM: Artificial
<220> FEATURE:
<223> OTHER INFORMATION: Beta - lactamase region reverse primer

<400> SEQUENCE: 24
tttcacaccg catatggtgc                                                    20

<210> SEQ ID NO 25
<211> LENGTH: 26
<212> TYPE: DNA
<213> ORGANISM: Artificial
<220> FEATURE:
<223> OTHER INFORMATION: Beta -  lactamase forward primer

<400> SEQUENCE: 25
aagtatgcat gagtaaactt ggtctg                                             26

<210> SEQ ID NO 26
<211> LENGTH: 25
<212> TYPE: DNA
<213> ORGANISM: Artificial
<220> FEATURE:
<223> OTHER INFORMATION: p3ZIq24 origin region reverse primer

<400> SEQUENCE: 26
actcatgcat actttagatt gattt                                              25

<210> SEQ ID NO 27
<211> LENGTH: 18
<212> TYPE: DNA
<213> ORGANISM: Artificial
<220> FEATURE:
<223> OTHER INFORMATION: p3ZIq24 origin region forward primer

<400> SEQUENCE: 27
agagtgcacc atatgcgg                                                      18
```